United States Patent
Fest et al.

Patent Number: 5,211,740
Date of Patent: May 18, 1993

[54] HERBICIDAL AMINOGUANIDINOAZINES

[75] Inventors: Christa Fest, Wuppertal; Rolf Kirsten, Monheim; Joachim Kluth, Langenfeld; Klaus-Helmut Müller, Duesseldorf; Hans-Jochem Riebel, Wuppertal; Hans-Joachim Santel, Leverkusen; Robert R. Schmidt, Bergisch-Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 840,358

[22] Filed: Feb. 24, 1992

Related U.S. Application Data

[62] Division of Ser. No. 354,537, May 19, 1989, Pat. No. 5,092,917.

[30] Foreign Application Priority Data

May 27, 1988 [DE] Fed. Rep. of Germany ....... 3818040

[51] Int. Cl.$^5$ ................. A01M 43/66; A01M 43/68; A01M 43/70; C07D 251/46
[52] U.S. Cl. ................. 504/230; 544/211; 544/212; 544/213; 544/205; 544/206; 544/207; 544/208; 544/209; 544/210; 544/196; 544/197; 544/198; 504/231; 504/232; 504/234
[58] Field of Search ....... 71/93, 90; 544/211, 544/212, 213, 205, 206, 207, 208, 209, 210, 196, 197, 198

[56] References Cited

U.S. PATENT DOCUMENTS

| | | | |
|---|---|---|---|
| 4,602,938 | 7/1986 | Moriya et al. | 71/90 |
| 4,725,303 | 2/1988 | Moriya et al. | 71/92 |
| 4,725,304 | 2/1988 | Diehr et al. | 544/330 |

FOREIGN PATENT DOCUMENTS

| | | |
|---|---|---|
| 0121082 | 10/1984 | European Pat. Off. |
| 0173319 | 3/1986 | European Pat. Off. |
| 0173320 | 3/1986 | European Pat. Off. |
| 0224078 | 6/1987 | European Pat. Off. |

Primary Examiner—John M. Ford
Attorney, Agent, or Firm—Sprung Horn Kramer & Woods

[57] ABSTRACT

Herbicidal aminoguanidinoazines of the formula

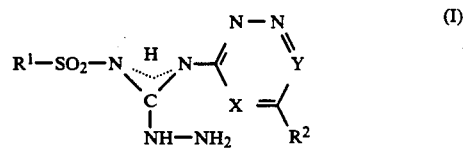

in which
R$^1$ stands for an optionally substituted radical from the series comprising alkyl, aralkyl, aryl and hetaryl,
R$^2$ stands for hydrogen, halogen, hydroxyl, alkyl, halogenoalkyl, alkoxyalkyl, alkoxy, halogenoalkoxy, alkylthio, halogenoalkylthio, amino, alkylamino or dialkylamino,
X stands for nitrogen or a —CH group,
Y stands for nitrogen or a —CR$^3$ group where R$^3$ stands for hydrogen, halogen, cyano, alkyl, formyl, alkyl-carbonyl or alkoxy-carbonyl, and
Z stands for nitrogen or a —CR$^4$ group where R$^4$ stands for hydrogen, halogen, hydroxyl, alkyl, halogenoalkyl, alkoxy, halogenoalkoxy, alkylthio, alkylamino or dialkylamino
and their salts, with the exception of the compounds N'-(4,6-dimethylpyrimidin-2-yl)-N"-amino-N"'-(2-diethylaminosulphonyl-phenylsulphonyl)-guanidine, N'-(4,6-dimethylpyrimidin-2-yl)-N"-amino-N"'-(2-methoxycarbonylphenylsulphonyl)-guanidine and N'-(4,6-dimethylpyrimidin-2-yl)-N"-amino-N"'-(2-methoxycarbonylthiophen-3-yl-sulphonyl)-guanidine and their salts.

6 Claims, No Drawings

HERBICIDAL AMINOGUANIDINOAZINES

This is a division, of application Ser. No. 354,537, filed May 19, 1989, now allowed as U.S. Pat. No. 5,092,917.

The invention relates to new aminoguanidinoazines, a process for their preparation, and their use as herbicides.

It has already been disclosed that certain substituted aminoguanidinoazines, such as, for example, N'-(4,6-dimethyl-pyrimidin-2-yl)-N''-acetylamino-N''''-(2-chloro-phenylsulphonyl)-guanidine, exhibit herbicidal properties (cf. EP-A 121,082). However, the herbicidal action of the previously known aminoguanidinoazines is not always completely satisfactory.

New aminoguanidinoazines of the general formula

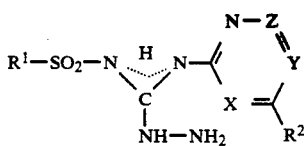

in which
R¹ stands for an optionally substituted radical from the series comprising alkyl, aralkyl, aryl and hetaryl,
R² stands for hydrogen, halogen, hydroxyl, alkyl, halogenoalkyl, alkoxyalkyl, alkoxy, halogenoalkoxy, alkylthio, halogenoalkylthio, amino, alkylamino or dialkylamino,
X stands for nitrogen or a —CH group,
Y stands for nitrogen or a —CR³ group where
R³ stands for hydrogen, halogen, cyano, alkyl, formyl, alkyl-carbonyl or alkoxy-carbonyl, and
Z stands for nitrogen or a —CR⁴ group, where
R⁴ stands for hydrogen, halogen, hydroxyl, alkyl, halogenoalkyl, alkoxy, halogenoalkoxy, alkylthio, alkylamino or dialkylamino,
and salts of compounds of the formula (I), have now been found, with the exception of the following compounds: N'-(4,6-dimethyl-pyrimidin-2-yl)-N''-amino-N''''-(2-diethylaminosulphonyl-phenylsulphonyl)-guanidine (cf. U.S. Pat. No. 4,725,303, Example 230); N'-(4,6-dimethyl-pyrimidin-2-yl)-N''-amino-N''''-(2-methoxycarbonyl-phenylsulphonyl)-guanidine (cf. U.S. Pat. No. 4,725, 303, Example 201) and N'-(4,6-dimethyl-pyrimidin-2-yl)-N''-amino-N''''-(2-methoxycarbonylthiophen-3-yl-sulphonyl)-guanidine (cf. EP-A 224,078, Example 27).

The general formula (I) stands for the individual possible tautomers of the formulae (IA), (IB) and (IC)

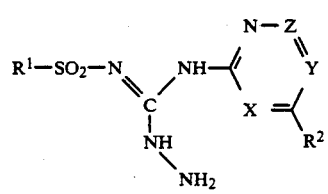

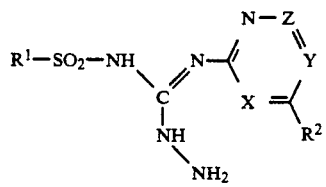

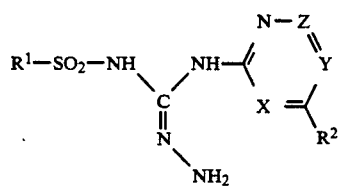

and for mixtures of these tautomers.

The new aminoguinidines of the general formula (I) are obtained when sulphonyl compounds of the general formula (II)

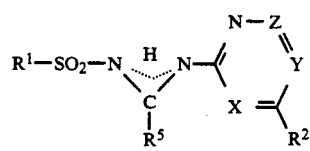

in which
R¹, R², X, Y and Z have the abovementioned meanings and
R⁵ stands for halogen or one of the leaving groups $R^6-SO_2-N(OR^7)-$ or $-Q-R^8$ mentioned below where
R⁶ has the meaning mentioned above for R¹ but does not necessarily have to be identical to R¹ in each individual case,
R⁷ stands for alkyl, alkenyl or aralkyl,
R⁸ stands for in each case optionally substituted alkyl, aralkyl or aryl and
Q stands for oxygen or sulphur,
are reacted with hydrazine or a hydrazine/water or hydrazine/acid adduct,
if appropriate in the presence of acid acceptor and if appropriate in the presence of a diluent, and if appropriate the resulting products are converted to salts by customary methods.

Some of the compounds of the formula (I) according to the invention can also be obtained as outlined below (R as indicated below for R¹²)

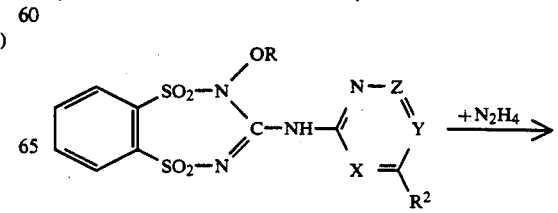

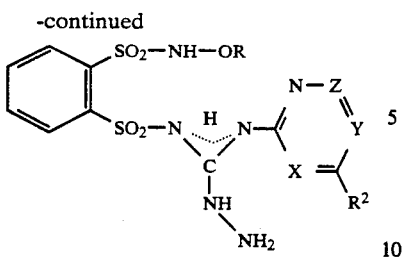

(for the reaction principle, see U.S. Pat. No. 4,659,364, EP-A 173,319).

The new aminoguanidinoazines of the general formula (I) are distinguished by powerful herbicidal activity.

Surprisingly, the new compounds of the general formula (I) show considerably more powerful herbicidal action than previously known aminoguanidinoazines with the same type of action.

The invention preferably relates to compounds of the formula (I) in which $R^1$ stands for the radical

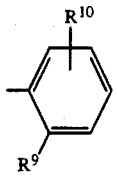

where $R^9$ and $R^{10}$ are identical or different and stand for hydrogen, fluorine, chlorine, bromine, iodine, cyano, nitro, $C_1$–$C_6$-alkyl [which is optionally substituted by fluorine, chlorine, bromine, cyano, carboxyl, $C_1$–$C_4$-alkoxycarbonyl, $C_1$–$C_4$-alkyl-aminocarbonyl, di-($C_1$–$C_4$-alkyl)-amino-carbonyl, hydroxyl, $C_1$–$C_4$-alkoxy, formyloxy, $C_1$–$C_4$-alkylcarbonyloxy, $C_1$–$C_4$-alkoxy-carbonyloxy, $C_1$–$C_4$-alkylamino-carbonyloxy, $C_1$–$C_4$-alkylthio, $C_1$–$C_4$-alkylsulphinyl, $C_1$–$C_4$-alkylsulphonyl, di-($C_1$–$C_4$-alkyl)-aminosulphonyl, $C_3$–$C_6$-cycloalkyl or phenyl], for $C_2$–$C_6$-alkenyl [which is optionally substituted by fluorine, chlorine, bromine, cyano, $C_1$–$C_4$-alkoxycarbonyl, carboxyl or phenyl], for $C_2$–$C_6$-alkinyl [which is optionally substituted by fluorine, chlorine, bromine, cyano, $C_1$–$C_4$-alkoxycarbonyl, carboxyl or phenyl], for $C_1$–$C_4$-alkoxy [which is optionally substituted by fluorine, chlorine, bromine, cyano, carboxyl, $C_1$–$C_4$-alkoxy-carbonyl, $C_1$–$C_4$-alkoxy, $C_1$–$C_4$-alkylthio, $C_1$–$C_4$-alkylsulphinyl or $C_1$–$C_4$-alkylsulphonyl], for $C_1$–$C_4$-alkylthio [which is optionally substituted by fluorine, chlorine, bromine, cyano, carboxyl, $C_1$–$C_4$-alkoxy-carbonyl, $C_1$–$C_4$-alkylthio, $C_1$–$C_4$-alkylsulphinyl or $C_1$–$C_4$-alkylsulphonyl], for $C_3$–$C_6$-alkenyloxy [which is optionally substituted by fluorine, chlorine, bromine, cyano or $C_1$–$C_4$-alkoxy-carbonyl], for $C_2$–$C_6$-alkenylthio [which is optionally substituted by fluorine, chlorine, bromine, cyano, nitro, $C_1$–$C_3$-alkylthio or $C_1$–$C_4$-alkoxycarbonyl], $C_3$–$C_6$-alkinyloxy, $C_3$–$C_6$-alkinylthio or for the radical —$S(O)_p$-$R^{11}$ where p stands for the numbers 1 or 2 and $R^{11}$ stands for $C_1$–$C_4$-alkyl [which is optionally substituted by fluorine, chlorine, bromine, cyano or $C_1$–$C_4$-alkoxy-carbonyl], $C_3$–$C_6$-alkenyl, $C_3$–$C_6$-alkinyl, $C_1$–$C_4$-alkoxy, $C_1$–$C_4$-alkoxy$C_1$–$C_4$-alkylamino, $C_1$–$C_4$-alkylamino, di-($C_1$–$C_4$-alkyl)-amino or for the radical —$NHOR^{12}$ where $R^{12}$ stands for $C_1$–$C_{12}$-alkyl [which is optionally substituted by fluorine, chlorine, cyano, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkylcarbonyl, $C_1$–$C_4$-alkoxy-carbonyl, $C_1$–$C_4$-alkylamino-carbonyl or di-($C_1$–$C_4$-alkyl)-amino-carbonyl], for $C_3$–$C_6$-alkenyl [which is optionally substituted by fluorine, chlorine or bromine], $C_3$–$C_6$-alkinyl, $C_3$–$C_6$-cycloalkyl, $C_3$–$C_6$-cycloalkyl-$C_1$–$C_2$-alkyl, phenyl-$C_1$–$C_2$-alkyl [which is optionally substituted by fluorine, chlorine, nitro, cyano, $C_1$–$C_4$-alkyl, $C_1$–$C_4$-alkoxy or $C_1$–$C_4$-alkoxy-carbonyl], for benzhydryl or for phenyl [which is optionally substituted by fluorine, chlorine, nitro, cyano, $C_1$–$C_4$-alkyl, trifluoromethyl, $C_1$–$C_4$-alkoxy, $C_1$–$C_2$-fluoroalkoxy, $C_1$–$C_4$-alkylthio, trifluoromethylthio or $C_1$–$C_4$-alkoxy-carbonyl], $R^9$ and $R^{10}$ furthermore stand for phenyl or phenoxy, for amino, $C_1$–$C_4$-alkylcarbonylamino, $C_1$–$C_4$-alkoxy-carbonylamino, $C_1$–$C_4$-alkylaminocarbonyl-amino, di-($C_1$–$C_4$-alkyl)-amino-carbonylamino, or for the radical —CO—$R^{13}$ where $R^{13}$ stands for $C_1$–$C_6$-alkyl, $C_1$–$C_6$-alkoxy, $C_3$–$C_6$-cycloalkoxy, $C_3$–$C_6$-alkenyloxy, $C_1$–$C_4$ alkylthio, $C_1$–$C_4$-alkylamino, $C_1$–$C_4$-alkoxyamino, $C_1$–$C_4$-alkoxy-$C_1$–$C_4$-alkyl-amino or di-($C_1$–$C_4$-alkyl)-amino [which are optionally substituted by fluorine and/or chlorine], $R^9$ and $R^{10}$ furthermore stand for $C_1$–$C_4$-alkylsulphonyloxy, di-($C_1$–$C_4$-alkyl)-aminosulphonylamino, thiazolyloxy or for the radical —CH═N-$R^{14}$ where $R^{14}$ stands for $C_1$–$C_6$-alkyl which is optionally substituted by fluorine, chlorine, cyano, carboxyl, $C_1$–$C_4$-alkoxy, $C_1$–$C_4$-alkylthio, $C_1$–$C_4$-alkylsulphinyl or $C_1$–$C_4$-alkysulphonyl, for benzyl which is optionally substituted by fluorine or chlorine, for $C_3$–$C_6$-alkenyl or $C_3$–$C_6$-alkinyl, each of which is optionally substituted by fluorine or chlorine, for phenyl which is optionally substituted by fluorine, chlorine, bromine, $C_1$–$C_4$-alkyl, $C_1$–$C_4$-alkoxy, trifluoromethyl, trifluoromethoxy or trifluoromethylthio, for $C_1$–$C_6$-alkoxy, $C_3$–$C_6$-alkenoxy, $C_3$–$C_6$-alkinoxy or benzyloxy, each of which is optionally substituted by fluorine and/or chlorine, for amino, $C_1$–$C_4$-alkylamino, di-($C_1$–$C_4$-alkyl)-amino, phenylamino, $C_1$–$C_4$-alkylcarbonyl-amino, $C_1$–$C_4$-alkoxy-carbonylamino, $C_1$–$C_4$-alkyl-sulphonylamino or for phenylsulphonylamino which is optionally substituted by fluorine, chlorine, bromine or methyl, where furthermore $R^1$ stands for the radical

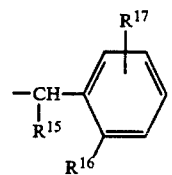

where $R^{15}$ stands for hydrogen or $C_1$–$C_4$-alkyl, $R^{16}$ and $R^{17}$ are identical or different and stand for hydrogen, fluorine, chlorine, bromine, nitro, cyano, $C_1$-$C_4$-alkyl [which is optionally substituted by fluorine and/or chlorine], $C_1$-$C_4$-alkoxy [which is optionally substituted by fluorine and/or chlorine], carboxyl, $C_1$-$C_4$-alkoxy-carbonyl, $C_1$-$C_4$-alkylsulphonyl or di-($C_1$-$C_4$-alkyl)aminosulphonyl; where furthermore $R^1$ stands for the radical

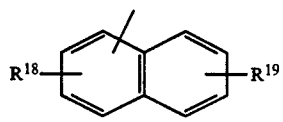

where $R^{18}$ and $R^{19}$ are identical or different and stand for hydrogen, fluorine, chlorine, bromine, nitro, cyano, $C_1$-$C_4$-alkyl [which is optionally substituted by fluorine and/or chlorine] or $C_1$-$C_4$-alkoxy [which is optionally substituted by fluorine and/or chlorine]; where furthermore $R^1$ stands for the radical

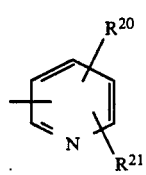

where $R^{20}$ and $R^{21}$ are identical or different and stand for hydrogen, fluorine, chlorine, bromine, nitro, cyano, $C_1$-$C_4$-alkyl [which is optionally substituted by fluorine and/or chlorine], $C_2$-$C_4$-alkenyl [which is optionally substituted by fluorine and/or chlorine], $C_1$-$C_4$-alkoxy [which is optionally substituted by fluorine and/or chlorine], for $C_1$-$C_4$-alkylthio, $C_1$-$C_4$-alkylsulphinyl or $C_1$-$C_4$-alkylsulphonyl [each of which is optionally substituted by fluorine and/or chlorine], and also for di-($C_1$-$C_4$-alkyl)-aminosulphonyl, $C_1$-$C_4$-alkoxy-carbonyl, dimethylaminocarbonyl or dioxolanyl; where furthermore $R^1$ stands for the radical

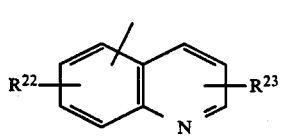

where $R^{22}$ and $R^{23}$ are identical or different and stand for hydrogen, fluorine, chlorine, bromine, $C_1$-$C_4$-alkyl [which is optionally substituted by fluorine and/or bromine], $C_1$-$C_4$-alkoxy [which is optionally substituted by fluorine and/or chlorine], for $C_1$-$C_4$-alkylthio, $C_1$-$C_4$-alkylsulphinyl or $C_1$-$C_4$-alkylsulphonyl [each of which is optionally substituted by fluorine and/or chlorine], or for di-($C_1$-$C_4$-alkyl)-aminosulphonyl; where furthermore $R^1$ stands for the radical

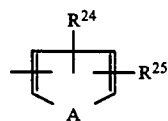

where $R^{24}$ and $R^{25}$ are identical or different and stand for hydrogen, fluorine, chlorine, bromine, cyano, nitro, $C_1$-$C_4$-alkyl [which is optionally substituted by fluorine, chlorine, $C_1$-$C_4$-alkoxy and/or $C_1$-$C_4$-halogenoalkoxy], $C_1$-$C_4$-alkoxy [which is optionally substituted by fluorine and/or chlorine, $C_1$-$C_4$-alkylthio, $C_1$-$C_4$-alkylsulphinyl or $C_1$-$C_4$-alkylsulphonyl [which is optionally substituted by fluorine and/or chlorine], di-($C_1$-$C_4$-alkyl)-amino-sulphonyl, $C_1$-$C_4$-alkoxy-carbonyl, dioxolanyl or 2-thiazolyl, and A stands for oxygen, sulphur or the group N-$Z^1$ where $Z^1$ stands for hydrogen, $C_1$-$C_4$-alkyl [which is optionally substituted by fluorine, chlorine, bromine or cyano], $C_3$-$C_6$-cycloalkyl, benzyl, phenyl [which is optionally substituted by fluorine, chlorine, bromine or nitro], $C_1$-$C_4$-alkyl-carbonyl, $C_1$-$C_4$-alkoxy-carbonyl or di-($C_1$-$C_4$-alkyl)-aminocarbonyl; where furthermore $R^1$ stands for the radical

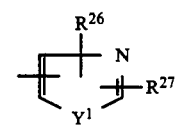

where $R^{26}$ stands for hydrogen, $C_1$-$C_5$-alkyl or halogen, $R^{27}$ stands for hydrogen or $C_1$-$C_5$-alkyl and $Y^1$ stands for sulphur or the group N-$R^{28}$ where $R^{28}$ stands for hydrogen or $C_1$-$C_5$-alkyl, where furthermore $R^1$ stands for the radical

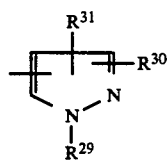

where $R^{29}$ stands for hydrogen, $C_1$-$C_4$-alkyl, phenyl or (iso)-quinolinyl, $R^{30}$ stands for hydrogen, halogen, cyano, nitro, $C_1$-$C_4$-alkyl [which is optionally substituted by fluorine and/or chlorine], $C_1$-$C_4$-alkoxy [which is optionally substituted by fluorine and/or chlorine], dioxolanyl or $C_1$-$C_4$-alkoxy-carbonyl and $R^{31}$ stands for hydrogen, halogen or $C_1$-$C_4$-alkyl, where furthermore $R^1$ stands for the radical

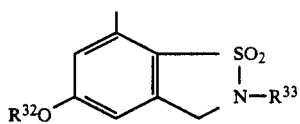

where
R$^{32}$ stands for C$_1$–C$_3$-alkyl and
R$^{33}$ stands for C$_1$–C$_4$-alkyl,
where furthermore
R$^1$ stands for the radical

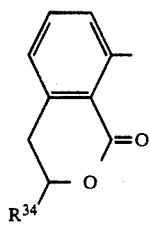

where
R$^{34}$ stands for hydrogen or methyl,
where furthermore
R$^1$ stands for the radical

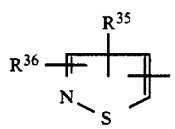

where
R$^{35}$ stands for hydrogen, halogen or C$_1$–C$_4$-alkyl and
R$^{36}$ stands for hydrogen, halogen, C$_1$–C$_4$-alkyl, C$_1$–C$_4$-halogenoalkyl, C$_1$–C$_4$-alkoxy or C$_1$–C$_4$-halogenoalkoxy,
in which furthermore
R$^2$ stands for hydrogen, fluorine, chlorine, bromine, C$_1$–C$_4$-alkyl, C$_1$–C$_4$-halogenoalkyl, C$_1$–C$_2$-alkoxy-C$_1$–C$_2$-alkyl, bis-(C$_1$–C$_2$-alkoxy)C$_1$–C$_2$-alkyl, C$_1$–C$_4$-alkoxy, C$_1$–C$_4$-halogenoalkoxy, C$_1$–C$_4$-alkylthio, C$_1$–C$_4$-halogenoalkylthio, amino, C$_1$–C$_4$-alkylamino, dimethylamino or diethylamino,
X stands for nitrogen or a —CH group,
Y stands for nitrogen or a —CR$^3$ group where
R$^3$ stands for hydrogen, fluorine, chlorine, bromine, cyano, methyl, formyl, acetyl, methoxycarbonyl or ethoxycarbonyl, and
Z stands for nitrogen or a —CR$^4$ group where
R$^4$ stands for hydrogen, fluorine, chlorine, bromine, C$_1$–C$_4$-alkyl, trifluoromethyl, C$_1$–C$_4$-alkoxy, difluoromethoxy, C$_1$–C$_4$-alkylthio, C$_1$–C$_4$-alkylamino, dimethylamino or diethylamino,
with the exception of N'-(4,6-dimethyl-pyrimidin-2-yl)-N''-amino-N'''-(2-diethylaminosulphonyl-phenylsulphonyl)-guanidine, N'-(4,6-dimethyl-pyrimidin-2-yl)-N''-amino-N'''-(2-methoxycarbonyl-phenylsulphonyl)-guanidine and N'-(4,6-dimethyl-pyrimidin-2-yl)-N''-amino-N'''-(2-methoxycarbonyl-thiophen-3-yl-sulphonyl)-guanidine.

In particular, the invention relates to compounds of the formula (I) in which
R$^1$ stands for the radical

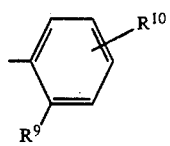

where
R$^9$ stands for fluorine, chlorine, bromine, methyl, trifluoromethyl, methoxy, difluoromethoxy, trifluoromethoxy, C$_1$–C$_3$-alkylthio, C$_1$–C$_3$-alkylsulphinyl, C$_1$–C$_3$-alkylsulphonyl, dimethylaminosulphonyl, diethylaminosulphonyl, N-methoxy-N-methylamino-sulphonyl, phenyl, phenoxy or C$_1$–C$_3$-alkoxycarbonyl and
R$^{10}$ stands for hydrogen or chlorine; where furthermore
R$^1$ stands for the radical

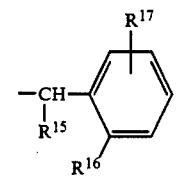

where
R$^{15}$ stands for hydrogen
R$^{16}$ stands for fluorine, chlorine, bromine, methyl, methoxy, ethoxy, difluoromethoxy, trifluoromethoxy, methoxycarbonyl, ethoxycarbonyl, methylsulphonyl or dimethylaminosulphonyl and
R$^{17}$ stands for hydrogen or chlorine;
where furthermore
R$^1$ stands for the radical

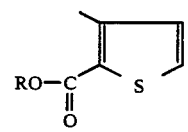

where
R stands for C$_1$–C$_2$-alkyl, or
R$^1$ stands for the radical

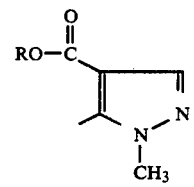

where
R stands for C$_1$–C$_2$-alkyl; in which furthermore
R$^2$ stands for hydrogen, fluorine, chlorine, bromine, methyl, dimethoxymethyl, trifluoromethyl, methoxy, ethoxy, difluoromethoxy, methylthio, ethylthio, amino, methylamino, ethylamino, dimethylamino, diethylamino or methoxymethyl,
X stands for nitrogen or a —CH group,
Y stands for nitrogen or a —CR$^3$ group where
R$^3$ stands for hydrogen, fluorine, chlorine or methyl, and Z stands for nitrogen or a —CR⁴ group where
R⁴ stands for hydrogen, fluorine, chlorine, bromine, methyl, ethyl, trifluoromethyl, methoxy, ethoxy, propoxy, isopropoxy, difluoromethoxy, methylthio, ethylthio, methylamino, ethylamino, dimethylamino or diethylamino, with the exception of N'-(4,6-dimethyl-pyrimidin-2-yl)-N''-amino-N'''-(2-diethylaminosulphonyl-phenylsulphonyl)guanidine, N'-(4,6-dimethyl-pyrimidin-2-yl)-N''-amino-N'''-(2-methoxycarbonyl-phenylsulphonyl)-guanidine and N'-(4,6-dimethyl-pyrimidin-2-yl)-N''-amino-N'''-(2-methoxycarbonyl-thiophen-3-ylsulphonyl)-guanidine.

The invention furthermore preferably relates to salts of compounds of the formula (I)
α) with protonic acids, such as, for example, hydrochloric acid, sulphuric acid, phosphoric acid, methanesulphonic acid, benzene- or p-toluenesulphonic acid, or naphthalene-mono- or -di-sulphonic acids, or
β) with bases, such as, for example, sodium hydroxide, sodium hydride, sodium amide, sodium carbonate, potassium hydroxide, potassium hydride, potassium amide, potassium carbonate, calcium hydroxide, calcium hydride, calcium amide or calcium carbonate, sodium $C_1$-$C_4$- or potassium $C_1$-$C_4$-alkoxides, ammonia, $C_1$-$C_4$-alkylamines, di-($C_1$-$C_4$-alkyl)-amines or tri-($C_1$-$C_4$-alkyl)-amines.

If N'-(4,6-dimethoxy-s-triazin-2-yl)-N''-methoxy-N'', N'''-bis-(2-bromo-phenylsulphonyl)-guanidine and hydrazine are used as starting substances, the course of the reaction in the process according to the invention can be outlined by the following equation:

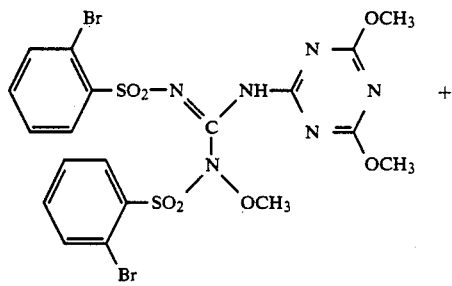

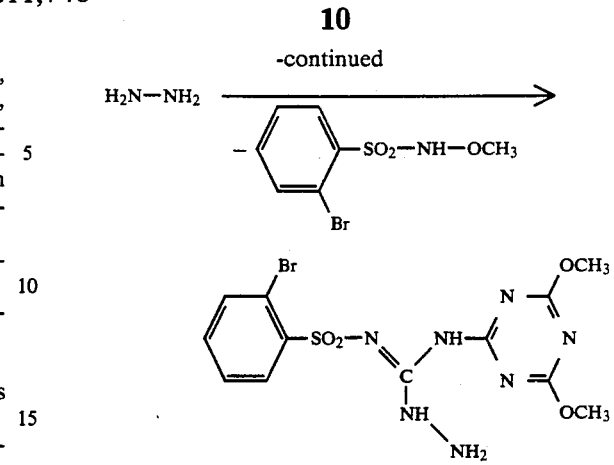

Formula (II) provides a general definition of the sulphonyl compounds to be used as starting substances in the process according to the invention. In formula (II), $R^1$, $R^2$, X, Y and Z preferably, or in particular, have those meanings which have already been mentioned above in connection with the description of the compounds of the formula (I) according to the invention as being preferred, or particularly preferred, for $R^1$, $R^2$, X, Y and Z, and
$R^5$ preferably stands for chlorine or one of the Leaving groups

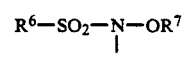

or -Q-$R^8$ mentioned below where
$R^6$ has the meaning preferably mentioned above for $R^1$ but does not necessarily have to be identical to $R^1$ in each individual case,
$R^7$ stands for $C_1$-$C_4$-alkyl, $C_3$-$C_4$-alkenyl or benzyl,
$R^8$ stands for $C_1$-$C_4$-alkyl which is optionally substituted by carboxyl, $C_1$-$C_4$-alkoxy-carbonyl or $C_1$-$C_4$-alkoxy, or for benzyl or phenyl, each of which is optionally substituted by fluorine, chlorine, bromine, $C_1$-$C_4$-alkyl or $C_1$-$C_4$-alkoxy, and
Q stands for oxygen or sulphur.

Examples of the starting substances of the formula (II) are listed in Table 1 below.

TABLE 1

Examples of the starting substances of the formula (II)

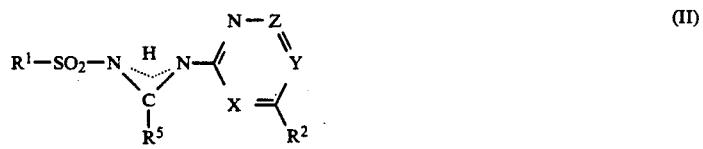

| $R^5$ | $R^1$ | $R^2$ | X | Y | Z |
|---|---|---|---|---|---|
| (2-Cl-phenyl-SO₂-N-OCH₃) | (2-Cl-phenyl) | $CH_3$ | N | CH | C—OCH₃ |

TABLE 1-continued

Examples of the starting substances of the formula (II)

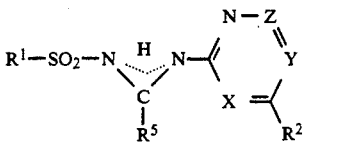

(II)

| R⁵ | R¹ | R² | X | Y | Z |
|---|---|---|---|---|---|
| 2-Br-C₆H₄-SO₂-N(OCH₃)- | 2-Br-C₆H₄- | OCH₃ | N | CH | C—OCH₃ |
| 2-F-C₆H₄-SO₂-N(OCH₃)- | 2-F-C₆H₄- | OCH₃ | N | CH | C—OCH₃ |
| 2-CF₃-C₆H₄-SO₂-N(OCH₃)- | 2-CF₃-C₆H₄- | OCH₃ | N | CH | C—OCH₃ |
| 2-OCHF₂-C₆H₄-SO₂-N(OCH₃)- | 2-OCHF₂-C₆H₄- | OCH₃ | N | CH | C—OCH₃ |
| 2-OCF₃-C₆H₄-SO₂-N(OCH₃)- | 2-OCF₃-C₆H₄- | OCH₃ | N | CH | C—OCH₃ |
| 2-COOCH₃-C₆H₄-SO₂-N(OCH₃)- | 2-COOCH₃-C₆H₄- | CH₃ | N | CH | C—CH₃ |
| 2-COOC₂H₅-C₆H₄-SO₂-N(OCH₃)- | 2-COOC₂H₅-C₆H₄- | CH₃ | N | CH | C—CH₃ |
| 2-COOCH₃-C₆H₄-SO₂-N(OCH₃)- | 2-COOCH₃-C₆H₄- | OCH₃ | N | CH | C—OCH₃ |
| 2-COOC₂H₅-C₆H₄-SO₂-N(OCH₃)- | 2-COOC₂H₅-C₆H₄- | OCH₃ | N | CH | C—OCH₃ |

TABLE 1-continued

Examples of the starting substances of the formula (II)

$$R^1-SO_2-N\underset{H}{\overset{H}{\cdots}}\underset{C}{\overset{}{\underset{R^5}{N}}}=\underset{X}{\overset{N-Z}{\underset{R^2}{\diagdown Y}}}$$ (II)

| R⁵ | R¹ | R² | X | Y | Z |
|---|---|---|---|---|---|
| 2-(SO₂—N(OCH₃))-phenyl, 1-COOCH₃ | 2-COOCH₃-phenyl | C₂H₅ | N | CH | C—OCH₃ |
| 2-(SO₂—N(OCH₃))-phenyl, 1-COOC₂H₅ | 2-COOC₂H₅-phenyl | C₂H₅ | N | CH | C—OCH₃ |
| 2-(SO₂—N(OCH₃))-phenyl, 1-COOCH₃ | 2-COOCH₃-phenyl | OCH₃ | N | CH | C—Cl |
| 2-(SO₂—N(OCH₃))-phenyl, 1-COOC₂H₅ | 2-COOC₂H₅-phenyl | OCH₃ | N | CH | C—Cl |
| 2-(SO₂—N(OCH₃))-phenyl, 1-OCF₃ | 2-OCF₃-phenyl | OCH₃ | N | CH | C—Cl |
| 2-(SO₂—N(OCH₃))-phenyl, 1-OCHF₂ | 2-OCHF₂-phenyl | OCH₃ | N | CH | C—Cl |
| 2-(SO₂—N(OCH₃))-phenyl, 1-SO₂—CH₃ | 2-SO₂—CH₃-phenyl | H | N | CH | C—CH₃ |
| 2-(SO₂—N(OCH₃))-phenyl, 1-SO₂—N(CH₃)₂ | 2-SO₂—N(CH₃)₂-phenyl | CH₃ | N | CH | C—OCH₃ |
| 2-(SO₂—N(OCH₃))-phenyl, 1-CH₃ | 2-CH₃-phenyl | OCH₃ | N | CH | C—OCH₃ |

TABLE 1-continued

Examples of the starting substances of the formula (II)

$$R^1-SO_2-N\overset{H}{\underset{\substack{\|\\C\\|\\R^5}}{\cdots}}N\overset{N-Z}{\underset{X}{\overset{\|}{=}}}\overset{}{\underset{R^2}{\overset{Y}{=}}}\quad\text{(II)}$$

| $R^5$ | $R^1$ | $R^2$ | X | Y | Z |
|---|---|---|---|---|---|
| 2-OCH3-C6H4-SO2-N(OCH3)- | 2-OCH3-C6H4- | CH3 | N | CH | C—OCH3 |
| 2-SCH3-C6H4-SO2-N(OCH3)- | 2-SCH3-C6H4- | OCH3 | N | CH | C—OCH3 |
| 2-[SO2-N(CH3)(OCH3)]-C6H4-SO2-N(OCH3)- | 2-[SO2-N(CH3)(OCH3)]-C6H4- | OCH3 | N | CH | C—OCH3 |
| 2-COOCH3-C6H4-SO2-N(OCH3)- | 2-COOCH3-C6H4- | CH3 | N | CH | C—OC2H5 |
| 2-COOCH3-C6H4-SO2-N(OCH3)- | 2-COOCH3-C6H4- | OCHF2 | N | CH | C—CH3 |
| 2-Br-C6H4-SO2-N(OCH3)- | 2-Br-C6H4- | CH3 | N | CH | C—SCH3 |
| 2-CF3-C6H4-SO2-N(OCH3)- | 2-CF3-C6H4- | CH3 | N | CH | C—N(CH3)2 |
| 2-COOCH3-C6H4-SO2-N(OCH3)- | 2-COOCH3-C6H4- | OCHF2 | N | CH | C—OCHF2 |

TABLE 1-continued

Examples of the starting substances of the formula (II)

$$R^1-SO_2-N\overset{H}{\underset{\underset{R^5}{|}}{\cdots}}\overset{}{\underset{}{C}}N\overset{N-Z}{\underset{X}{=}}\overset{}{\underset{R^2}{Y}}\quad (II)$$

| R⁵ | R¹ | R² | X | Y | Z |
|---|---|---|---|---|---|
| 2-C₆H₅-C₆H₄-SO₂-N(OCH₃)- | 2-C₆H₅-C₆H₄- | OCH₃ | N | CH | C—OCH₃ |
| 2-C₆H₅-C₆H₄-SO₂-N(OCH₃)- | 2-C₆H₅-C₆H₄- | OCH₃ | N | N | C—OCH₃ |
| 2-Cl-C₆H₄-SO₂-N(OCH₃)- | 2-Cl-C₆H₄- | CH₃ | N | N | C—OCH₃ |
| 2-OCHF₂-C₆H₄-SO₂-N(OCH₃)- | 2-OCHF₂-C₆H₄- | OCH₃ | N | N | C—OCH₃ |
| 2-OCF₃-C₆H₄-SO₂-N(OCH₃)- | 2-OCF₃-C₆H₄- | OCH₃ | N | N | C—OCH₃ |
| 2-COOCH₃-C₆H₄-SO₂-N(OCH₃)- | 2-COOCH₃-C₆H₄- | CH₃ | N | N | C—OCH₃ |
| 2-COOCH₃-C₆H₄-SO₂-N(OCH₃)- | 2-COOCH₃-C₆H₄- | OCH₃ | N | N | C—OCH₃ |
| 2-Br-C₆H₄-SO₂-N(OCH₃)- | 2-Br-C₆H₄- | CH₃ | N | N | C—CH₃ |
| 2-CF₃-C₆H₄-SO₂-N(OCH₃)- | 2-CF₃-C₆H₄- | CH₃ | N | N | C—Cl |

TABLE 1-continued

Examples of the starting substances of the formula (II)

$$R^1-SO_2-N\underset{H}{\overset{}{\underset{|}{C}}}N=\overset{N-Z}{\underset{X}{\overset{}{\underset{}{C}}}}\overset{}{\underset{R^2}{\overset{Y}{=}}}$$ (II)

| R⁵ | R¹ | R² | X | Y | Z |
|---|---|---|---|---|---|
| 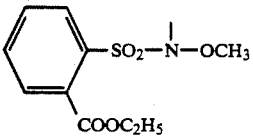 2-(COOC₂H₅)-C₆H₄-SO₂-N(OCH₃)- | 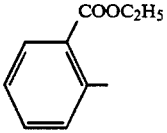 2-(COOC₂H₅)-C₆H₄- | OCH₃ | N | N | C—OCH₃ |
|  2-F-C₆H₄-SO₂-N(OCH₃)- | 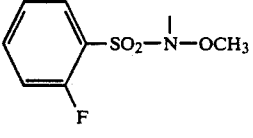 2-F-C₆H₄- | OCH₃ | N | N | C—OCH₃ |
| 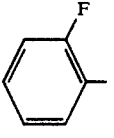 2-(SC₂H₅)-C₆H₄-SO₂-N(OCH₃)- |  2-(SC₂H₅)-C₆H₄- | OCH₃ | N | N | C—OCH₃ |
| 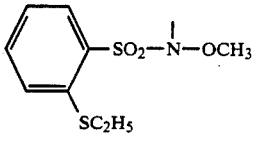 2-(COOCH₃)-C₆H₄-SO₂-N(OCH₃)- | 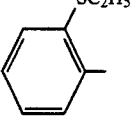 2-(COOCH₃)-C₆H₄-CH₂- | OCH₃ | N | CH | C—OCH₃ |
|  2-(OCF₃)-C₆H₄-CH₂-SO₂-N(OCH₃)- | 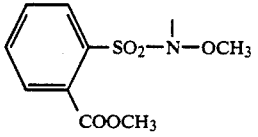 2-(OCF₃)-C₆H₄-CH₂- | OCH₃ | N | CH | C—OCH₃ |
| —OC₆H₅ | 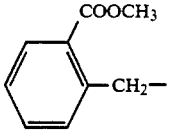 2-Cl-C₆H₄- | CH₃ | N | CH | C—CH₃ |
| —OCH₃ |  2-Cl-C₆H₄- | CH₃ | N | CH | C—OCH₃ |
| —SCH₃ | 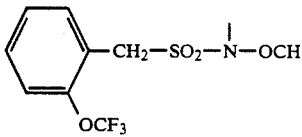 2-Cl-C₆H₄- | OCH₃ | N | CH | C—OCH₃ |
| —SC₆H₅ | 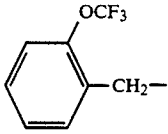 2-Cl-C₆H₄- | OCH₃ | N | CH | C—OCH₃ |

TABLE 1-continued

Examples of the starting substances of the formula (II)

$$R^1-SO_2-N\underset{H}{\overset{}{\underset{\underset{R^5}{|}}{C}}}N=C\underset{X}{\overset{N-Z}{\underset{}{\diagdown}}}\underset{R^2}{\overset{}{Y}} \quad (II)$$

| R⁵ | R¹ | R² | X | Y | Z |
|---|---|---|---|---|---|
| 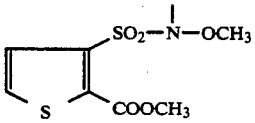 | 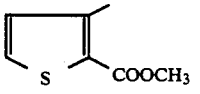 | CH₃ | N | N | C—OCH₃ |
| 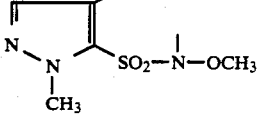 |  | OCH₃ | N | CH | C—OCH₃ |
| 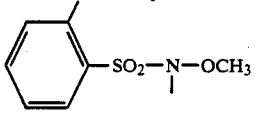 |  | OCH₃ | N | CH | C—OCH₃ |
| Cl | 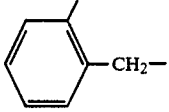 | OCH₃ | N | CH | C—OCH₃ |
| —OC₆H₅ | 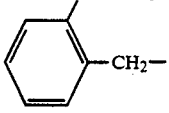 | OCH₃ | N | CH | C—OCH₃ |
| —SC₆H₅ | 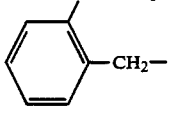 | OCH₃ | N | CH | C—OCH₃ |
| Cl | 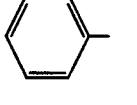 | CH₃ | N | N | C—OCH₃ |
| 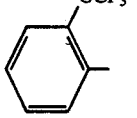 | 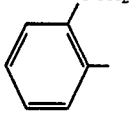 | CH₃ | N | N | C—OCH₃ |
| O—C₆H₅ | 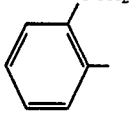 | CH₃ | N | N | C—OCH₃ |

TABLE 1-continued

Examples of the starting substances of the formula (II)

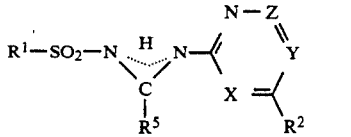

(II)

| R⁵ | R¹ | R² | X | Y | Z |
|---|---|---|---|---|---|
| 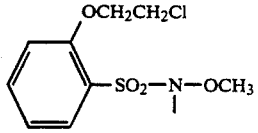 2-(OCH₂CH₂Cl), 4-(SO₂-N(CH₃)-OCH₃)-phenyl | 2-(OCH₂CH₂Cl)-phenyl | CH₃ | N | N | C—OCH₃ |
| S—C₆H₅ | 4-Cl-2-(COO—CH(CH₃)₂)-phenyl | CH₃ | N | N | C—OCH₃ |
| S—CH₃ | 4-Cl-2-(COO—CH(CH₃)₂)-phenyl | CH₃ | N | N | O—CH₃ |
| 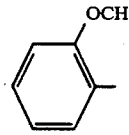 2-(COOC₂H₅), 4-(CHF₂O), 6-(SO₂-N(CH₃)-OCH₃)-phenyl | 2-(COOC₂H₅), 4-(CHF₂O)-phenyl | OCH₃ | N | CH | O—CH₃ |
| OCH₃ | 2-(OCH₂CH₂—OCH₃)-phenyl | OCH₃ | N | N | O—CH₃ |
| O—C₆H₅ | 2-(OCH₂CH₂—OCH₃)-phenyl | OCH₃ | N | N | O—CH₃ |
| S—CH₃ | 2-(COOCH₃)-phenyl | CH(OCH₃)₂ | N | CH | O—CH₃ |
| S—C₆H₅ | 2-(COOCH₃)-phenyl | CH(OCH₃)₂ | N | CH | O—CH₃ |
| S—CH₃ | 2-(COOCH₃)-phenyl | NH—CH₃ | N | N | O—C₂H₅ |

TABLE 1-continued

Examples of the starting substances of the formula (II)

$$R^1-SO_2-N\overset{H}{\underset{\underset{R^5}{|}}{C}}N\overset{N-Z}{\underset{X}{\overset{\|}{\underset{R^2}{C}}}}Y$$  (II)

| $R^5$ | $R^1$ | $R^2$ | X | Y | Z |
|---|---|---|---|---|---|
| [2-(COOCH₃)-phenyl-SO₂-N(OCH₃)-] | [2-(COOCH₃)-phenyl] | NH—CH₃ | N | N | O—C₂H₅ |
| S—CH₃ | [isochroman-1-one-8-yl-ethyl] | NH—CH₃ | N | N | O—C₂H₅ |
| S—CH₂—C₆H₅ | [3-methyl-isochroman-1-one-8-yl-methyl with CH₃] | NH—CH₃ | N | N | O—C₂H₅ |
| O—CH₃ | [5-CH₃O, 3-I, 2-(CH₂—N(C₄H₉-n)—SO₂—)-phenyl] | OCH₃ | N | CH | O—CH₃ |
| O—C₆H₅ | [5-CH₃O, 3-I, 2-(CH₂—N(C₄H₉-n)—SO₂—)-phenyl] | CH₃ | N | CH | O—CH₃ |
| S—CH₃ | [pyrazolo-isoquinoline with COOC₂H₅] | OCH₃ | N | CH | O—CH₃ |
| [pyrazolo-quinoline with COOC₂H₅ and CH₂—N—OCH₃] | [pyrazolo-quinoline with COOC₂H₅] | OCH₃ | N | CH | O—CH₃ |
| [3-CON(CH₃)₂-pyridin-2-yl-SO₂—N—OCH₃] | [3-CON(CH₃)₂-pyridin-2-yl] | OCH₃ | N | CH | O—CH₃ |

TABLE 1-continued

Examples of the starting substances of the formula (II)

$$R^1-SO_2-N\underset{R^5}{\overset{H}{\underset{C}{\vphantom{|}}}}N-\overset{N-Z}{\underset{X=\underset{R^2}{\vphantom{|}}}{\vphantom{|}}}Y \qquad (II)$$

| $R^5$ | $R^1$ | $R^2$ | X | Y | Z |
|---|---|---|---|---|---|
| ![pyridine with CON(CH3)2, H3C, N, SO2-N-OCH3] | ![pyridine with CON(CH3)2, H3C, N] | OCH$_3$ | N | CH | O—CH$_3$ |
| S—CH$_2$—C$_6$H$_5$ | ![pyridine with CON(CH3)2, Cl, N] | OCH$_3$ | N | CH | O—CH$_3$ |

The starting substances of the formula (II) are known and/or can be prepared by processes known per se (cf. EP-A 5,986, EP-A 24,215, EP-A 121,082, EP-A 172,957, EP-A 173,321, EP-A 173,956, EP-A 224,078, DE-OS (German Published Specification) 3,634,928 and DE-OS (German Published Specification) 3,634,929).

The process according to the invention is carried out using hydrazine or a hydrazine/water or hydrazine/acid adduct. Virtually anhydrous hydrazine or hydrazine hydrate and also hydrazine adducts with mineral acids, such as, for example, hydrazine mono-hydrochloride or hydrazine dihydrochloride and hydrazine sulphate are preferably suitable.

These compounds are known chemicals for synthesis.

The process according to the invention for the preparation of the new aminoguanidinoazines of the formula (I) is preferably carried out using diluents. Suitable diluents in this process are preferably water and/or polar organic solvents, such as methanol, ethanol, isopropanol, butanol, isobutanol, sec-butanol, tert-butanol, glycol dimethyl ether, diglycol dimethyl ether, tetrahydrofuran, dioxane, methyl acetate, ethyl acetate, acetonitrile, propionitrile, dimethylformamide, dimethylacetamide, N-methylpyrrolidone, dimethyl sulphoxide and tetramethylene sulphone.

Acid acceptors which can be used in the process according to the invention are all acid-binding agents which can customarily be used for reactions of this type. Alkali metal hydroxides, such as, for example, sodium hydroxide and potassium hydroxide, alkaline earth metal hydroxides, such as, for example, calcium hydroxide, alkali metal carbonates and alkali metal alkoxides, such as sodium carbonate, potassium carbonate, sodium tert-butoxide and potassium tert-butoxide, furthermore aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO) are preferably suitable.

In the process according to the invention, the reaction temperatures can be varied within a relatively wide range. In general, the process is carried out at temperatures between −20° C. and +80° C., preferably at temperatures between 0° C. and 50° C.

The process according to the invention is generally carried out under atmospheric pressure.

For carrying out the process according to the invention, between 1 and 3 moles, preferably between 1.0 and 1.5 moles, of hydrazine or hydrazine/water adduct or hydrazine/acid adduct are generally employed per mole of sulphonyl compound of the formula (II).

In general, the reactants are combined at room temperature or with ice cooling, and the reaction mixture is stirred until the reaction is complete, if necessary at increased temperature. The products of the formula (I) are generally obtained after cooling in the form of crystals and can be isolated by filtering off with suction.

If desired, salts can be prepared from the compounds of the general formula (I) according to the invention. Such salts are obtained in a simple manner by customary salt formation methods, for example by dissolving or dispersing a compound of the formula (I) in a suitable solvent, such as, for example, water, methanol, ethanol or acetone, and adding a suitable acid or base. The salts can then be isolated by concentrating or filtering off with suction, if necessary after stirring over a relatively long period.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in their formulations, can also be used for combating weeds, as mixtures with known herbicides finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione AMETHYDIONE) or N-(2-benzothiazolyl)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugar beets, and 4-amino-6-(1,1-dimethylethyl)-3-methylthio-1,2,4-triazin-5(4H)-one (METRIBUZIN) for combating weeds in soy beans; furthermore also 2,4-dichlorophenoxyacetic acid (2,4-D); 4-(2,4-dichlorophenoxy)-butyric acid (2,4-DB); 2,4-dichlorophenoxypropionic acid (2,4-DP); 2,6-dichlorobenzonitrile (DICHLOBENIL); 4-amino-6-t-butyl-3-ethylthio-1,2,4-triazin-5(4H)-one (ETHIOZIN); N-phosphonomethyl-glycine (GLYPHOSATE); 3-cyclohexyl-6-dimethylamino-1-methyl-1,3,5-triazine-2,4-dione (HEXAZINONE); 2-(4,5-dihydro-4-methyl-4-isopropyl-5-oxo-1H-imidazol-2-yl)-pyridine-3-carboxylic acid (IMAZAPYR); (2-methyl-4-chlorophenoxy)acetic acid (MCPA); (4-chloro-2-methylphenoxy)-propionic acid (MCPP); N-methyl-2-(1,3-benzothiazol-2-yloxy)acetanilide (MEFENACET); 2-chloro-4,6-bis-(ethylamino)-1,3,5-triazine (SIMAZIN) and methyl 2-{[(4,6-dimethyl-2-pyrimidinyl)-amino-carbonyl]-aminosulphonyl}-benzoate (SULFOMETURON).

Further suitable herbicides for the mixtures, especially for combating weeds in cereals, are known herbicides (designated by their common names), such as DICLOFOP, FENOXAPROP, PENDIMETHALIN, BIFENOX, CHLORTOLURON, ISO-PROTURON, IMAZAMETHABENZ, IOXYNIL, CHLORSULFURON, METSULFURON, SULFMETURON, THIAMETURON, TRIALLAT, TERBUTRYNE, BENTAZON and/or PYRIDATE (designated by their common names).

Surprisingly, some mixtures also show synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering. The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

Example 1

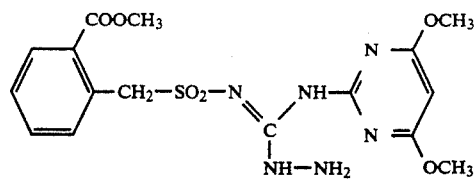

1.3 g (0.025 mol) of hydrazine hydrate are added, initially at 20° C., with stirring to a suspension of 15.9 g (0.025 mol) of N'-(4,6-dimethoxy-pyrimidin-2-yl)-N''-methoxy-N''-(2-methoxycarbonyl-phenylsulphonyl)-N'''-(2-methoxycarbonyl-benzylsulphonyl)-guanidine in 100 ml of methanol, during which process the reaction mixture warms to 30° C. and a clear solution forms. The product, which deposits in the form of crystals after stirring for 4 hours at 20° C. to 30° C., is isolated by filtering off with suction.

9.5 g (89% of theory) of N'-(4,6-dimethoxypyrimidin-2-yl)-N''-amino-N'''-(2-methoxycarbonyl-benzylsulphonyl)guanidine of melting point 166° C. are obtained.

The compounds of the formula (I) listed in Table 2 below can be prepared in analogy to Example 1 and following the general description of the process according to the invention.

TABLE 2

Examples of the compounds of the formula (I)

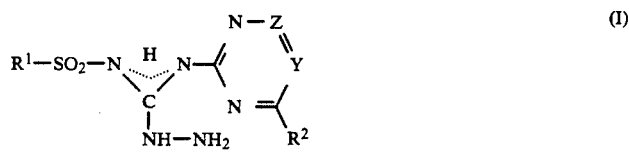

(I)

| Example No. | $R^1$ | $R^2$ | X | Y | Z | Melting point (°C.) |
|---|---|---|---|---|---|---|
| 2 | 2-OCF₃-phenyl | OCH₃ | N | CH | C—OCH₃ | 134 |
| 3 | 2-COOCH₃-phenyl | OCH₃ | N | CH | C—OCH₃ | 159 |
| 4 | 2-OCHF₂-phenyl | CH₃ | N | CH | C—CH₃ | 98 |
| 5 | 2-OCF₃-phenyl | CH₃ | N | N | C—OCH₃ | amorphous |

TABLE 2-continued

Examples of the compounds of the formula (I)

$$R^1-SO_2-N\overset{H}{\underset{\underset{NH-NH_2}{|}}{N}}\overset{N-Z}{\underset{N}{\overset{}{C}}}\overset{}{\underset{R^2}{Y}} \quad (I)$$

| Example No. | R¹ | R² | X | Y | Z | Melting point (°C.) |
|---|---|---|---|---|---|---|
| 6 | 2-(OCF₃)-phenyl | OCH₃ | N | N | C—OCH₃ | amorphous |
| 7 | 2-Cl-phenyl | CH₃ | N | CH | C—OCH₃ | 166 |
| 8 | 3-(COOC₂H₅)-5-methyl-1-methylpyrazol-4-yl | CH₃ | N | CH | C—CH₃ | 105 |
| 9 | 3-(COOC₂H₅)-5-methyl-1-methylpyrazol-4-yl | CH₃ | N | N | C—CH₃ | 102 |
| 10 | 2-Br-phenyl | CH₃ | N | CH | C—CH₃ | |
| 11 | 2-(COOCH₃)-phenyl | CH₃ | N | N | C—OCH₃ | |
| 12 | 2-(COOCH₃)-phenyl | OCH₃ | N | CH | C—OCH₃ | |
| 13 | 2-(COOC₂H₅)-phenyl | CH₃ | N | CH | C—OCH₃ | |
| 14 | 2-(COOC₂H₅)-phenyl | OCH₃ | N | CH | C—OCH₃ | |

TABLE 2-continued

Examples of the compounds of the formula (I)

$$R^1-SO_2-N\underset{\underset{NH-NH_2}{|}}{\overset{H}{\underset{C}{|}}}N\underset{}{\overset{}{=}}\underset{\overset{|}{R^2}}{\overset{N-Z}{\underset{N}{\overset{\|}{\diagdown}}}\overset{}{\diagup}Y}$$ (I)

| Example No. | R¹ | R² | X | Y | Z | Melting point (°C.) |
|---|---|---|---|---|---|---|
| 15 | 2-(OCF₃)-benzyl (-CH₂-C₆H₄-OCF₃) | OCH₃ | N | CH | C—OCH₃ | |
| 16 | 2-F-phenyl | OCH₃ | N | N | C—OCH₃ | |
| 17 | 2-OCF₃-phenyl | C₂H₅ | N | CH | C—OCH₃ | |
| 18 | 2-COOC₂H₅-phenyl | CH₃ | N | N | C—OCH₃ | |
| 19 | 2-COOC₂H₅-phenyl | OCH₃ | N | N | C—OCH₃ | |
| 20 | 2-Cl-phenyl | CH₃ | N | N | C—OCH₃ | |
| 21 | 2-Cl-phenyl | OCH₃ | N | N | C—OCH₃ | 175 |
| 22 | 2-Br-phenyl | OCH₃ | N | N | C—OCH₃ | |
| 23 | 2-COOC₂H₅-phenyl | CH₃ | N | CH | C—CH₃ | |

TABLE 2-continued

Examples of the compounds of the formula (I)

$$R^1-SO_2-N\overset{H}{\underset{\underset{NH-NH_2}{|}}{C}}N\overset{N=Z}{\underset{N}{\diagdown}}\overset{Y}{\underset{R^2}{\diagup}}\quad(I)$$

| Example No. | R¹ | R² | X | Y | Z | Melting point (°C.) |
|---|---|---|---|---|---|---|
| 24 | 2-CF₃-phenyl | CH₃ | N | CH | C—CH₃ | |
| 25 | 2-CF₃-phenyl | OCH₃ | N | CH | C—OCH₃ | |
| 26 | 2-CF₃-phenyl | CH₃ | N | N | C—OCH₃ | |
| 27 | 2-OCHF₂-phenyl | OCH₃ | N | CH | C—OCH₃ | |
| 28 | 2-OCHF₂-phenyl | OCH₃ | N | N | C—OCH₃ | |
| 29 | 2-OCHF₂-benzyl | OCH₃ | N | CH | C—OCH₃ | |
| 30 | 2-OCHF₂-benzyl | OCH₃ | N | N | C—OCH₃ | |
| 31 | 2-COOCH₃-phenyl | C₂H₅ | N | N | C—OCH₃ | |
| 32 | 2-OCF₃-phenyl | CH₃ | N | CH | C—OC₂H₅ | |

TABLE 2-continued

Examples of the compounds of the formula (I)

$$R^1-SO_2-N\overset{H}{\underset{C}{\cdots}}N\overset{N-Z}{\underset{N}{=}}\overset{}{\underset{R^2}{Y}}$$ (I)

$$\text{NH}-\text{NH}_2$$

| Example No. | R¹ | R² | X | Y | Z | Melting point (°C.) |
|---|---|---|---|---|---|---|
| 33 | 2-(COOCH₃)-C₆H₄-CH₂- | OCH₃ | N | N | C—OCH₃ | |
| 34 | 1-methyl-5-methyl-4-(COOC₂H₅)-pyrazol-3-yl | OCH₃ | N | CH | C—OCH₃ | 125 |
| 35 | 3-methyl-2-(COOCH₃)-thiophen-... | CH₃ | N | N | C—OCH₃ | |
| 36 | 3-methyl-2-(COOCH₃)-thiophen-... | OCH₃ | N | N | C—OCH₃ | |
| 37 | 1-methyl-5-methyl-4-(COOCH₃)-pyrazol-3-yl | OCH₃ | N | N | C—OCH₃ | |
| 38 | 2-(C₆H₅)-C₆H₄- | OCH₃ | N | CH | C—OCH₃ | |
| 39 | 2-(C₆H₅)-C₆H₄- | OCH₃ | N | N | C—OCH₃ | 143 |
| 40 | 2-(COOC₂H₅)-C₆H₄- | OCH₃ | N | CH | C—Cl | |
| 41 | 2-(CH₃)-C₆H₄- | CH₃ | N | N | C—OCH₃ | |

TABLE 2-continued
Examples of the compounds of the formula (I)
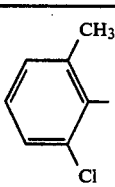
| Example No. | R¹ | R² | X | Y | Z | Melting point (°C.) |
|---|---|---|---|---|---|---|
| 42 |  (2-CH₃, 3-Cl phenyl) | CH₃ | N | CH | C—CH₃ | |
| 43 | 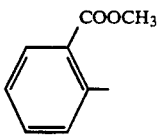 (2-COOCH₃ phenyl) | CF₃ | N | CH | C—OCH₃ | |
| 44 |  (2-COOCH₃ phenyl) | CH₃ | N | CH | C—OCHF₂ | |
| 45 | 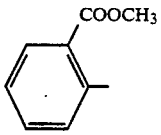 (2-COOCH₃ phenyl) | OCH₃ | N | CH | C—OCHF₂ | |
| 46 |  (2-COOCH₃ phenyl) | OCHF₂ | N | CH | C—OCHF₂ | |
| 47 | 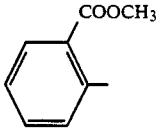 (2-COOCH₃ phenyl) | NHCH₃ | N | N | C—OC₂H₅ | |
| 48 |  (2-COOCH₃ phenyl) | NHC₂H₅ | N | N | C—OCH₃ | |
| 49 | 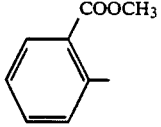 (2-COOCH(CH₃)₂, 4-Cl phenyl) | CH₃ | N | N | C—OCH₃ | |

TABLE 2-continued

Examples of the compounds of the formula (I)

$$R^1-SO_2-N\overset{H}{\underset{\underset{NH-NH_2}{|}}{C}}N=\overset{N-Z}{\underset{N}{\diagdown}}\overset{}{\underset{R^2}{\diagup}}Y$$ (I)

| Example No. | R¹ | R² | X | Y | Z | Melting point (°C.) |
|---|---|---|---|---|---|---|
| 50 | 2-COOC₂H₅-4-OCHF₂-phenyl | OCH₃ | N | CH | C—OCH₃ | |
| 51 | 2-(OCH₂CH₂—Cl)-phenyl | CH₃ | N | N | C—OCH₃ | |
| 52 | 2-(OCH₂CH₂—OCH₃)-phenyl | OCH₃ | N | N | C—OCH₃ | |
| 53 | 2-COOC₂H₅-phenyl | Cl | N | CH | C—OCH₃ | |
| 54 | 2-COOCH₃-phenyl | CH(OCH₃)₂ | N | CH | C—OCH₃ | |
| 55 | isochroman-1-on-8-yl | NHCH₃ | N | N | C—OC₂H₅ | |
| 56 | 3-methyl-isochroman-1-on-8-yl | NHCH₃ | N | N | C—OC₂H₅ | |
| 57 | 5-CH₃O-3-CH₃-2-(N-C₄H₉-n)(SO₂)-benzyl | OCH₃ | N | CH | C—OCH₃ | |

TABLE 2-continued

Examples of the compounds of the formula (I)

$$R^1-SO_2-N\overset{H}{\underset{\underset{NH-NH_2}{|}}{\overset{|}{C}}}N\overset{N-Z}{\underset{N}{\overset{\|}{\underset{R^2}{\longleftarrow}}}}Y$$  (I)

| Example No. | R¹ | R² | X | Y | Z | Melting point (°C.) |
|---|---|---|---|---|---|---|
| 58 | 1-(isoquinolin-1-yl)-3-methyl-4-ethoxycarbonyl-pyrazole | OCH₃ | N | CH | C—OCH₃ | |
| 59 | 1-(isoquinolin-1-yl)-3-methyl-4-ethoxycarbonyl-pyrazole | OCH₃ | N | N | C—OCH₃ | |
| 60 | 2-methyl-3-(N,N-dimethylcarbamoyl)pyridine | OCH₃ | N | CH | C—OCH₃ | |
| 61 | 2,6-dimethyl-3-(N,N-dimethylcarbamoyl)pyridine | OCH₃ | N | CH | C—OCH₃ | |
| 62 | 2-methyl-6-chloro-3-(N,N-dimethylcarbamoyl)pyridine | OCH₃ | N | CH | C—OCH₃ | |
| 63 | 2-(trifluoromethoxy)benzyl | OCH₃ | N | N | C—OCH₃ | |
| 64 | 2-(trifluoromethoxy)benzyl | CH₃ | N | N | C—OCH₃ | |
| 65 | 2-(trifluoromethoxy)benzyl | CH₃ | N | N | C—CH₃ | |
| 66 | 2-(trifluoromethoxy)benzyl | NHCH₃ | N | N | C—OC₂H₅ | |

TABLE 2-continued

Examples of the compounds of the formula (I)

$$R^1-SO_2-N\overset{H}{\underset{\underset{NH-NH_2}{|}}{C}}N\overset{N-Z}{\underset{N}{\overset{\|}{=}}}\overset{Y}{\underset{R^2}{=}}$$ (I)

| Example No. | R¹ | R² | X | Y | Z | Melting point (°C.) |
|---|---|---|---|---|---|---|
| 67 | 2-(OCF₃)-benzyl (-CH₂-C₆H₄-OCF₃) | C₂H₅ | N | N | C—OCH₃ | |
| 68 | 2-(OCF₃)-benzyl | CH₃ | N | N | C—OC₂H₅ | |
| 69 | 2-(OCHF₂)-benzyl | CH₃ | N | N | C—OCH₃ | |
| 70 | 2-(OCHF₂)-benzyl | CH₃ | N | N | C—CH₃ | |
| 71 | 2-(OCHF₂)-benzyl | NHCH₃ | N | N | C—OC₂H₅ | |
| 72 | 2-(OCHF₂)-benzyl | C₂H₅ | N | N | C—OCH₃ | |
| 73 | 2-(OCHF₂)-benzyl | CH₃ | N | N | C—OC₂H₅ | |
| 74 | 2-(OCF₃)-phenyl | CF₃ | N | CH | C—OCH₃ | |
| 75 | 3-methyl-2-(methoxycarbonyl)thiophene | OCHF₂ | N | CH | C—OCHF₂ | |

TABLE 2-continued

Examples of the compounds of the formula (I)

$$R^1-SO_2-N\overset{H}{\underset{C}{\overset{|}{N}}}\overset{}{\underset{NH-NH_2}{N}}=\overset{N-Z}{\underset{N}{\overset{\|}{\underset{R^2}{Y}}}}\quad(I)$$

| Example No. | R[1] | R[2] | X | Y | Z | Melting point (°C.) |
|---|---|---|---|---|---|---|
| 76 | 4-(1,3-dioxolan-2-yl)-1-methylpyrazol-3-yl | OCH₃ | N | CH | C—OCH₃ | |
| 77 | 3-methyl-4-(2,2,2-trifluoroethoxy)isothiazol-5-yl | OCH₃ | N | CH | C—OCH₃ | |
| 78 | 3-methyl-4-(2,2,2-trichloroethoxy)isothiazol-5-yl | OCH₃ | N | N | C—OCH₃ | |
| 79 | 2-methyl-3-(thiazol-2-yl)thien-3-yl | OCH₃ | N | CH | C—OCH₃ | |
| 80 | 2-methyl-3-(OCHF—CF₂—OCH₃)thien-3-yl | OCH₃ | N | N | C—OCH₃ | |
| 81 | 2-methyl-3-(CH₂—O—CH₂—CF₃)thien-3-yl | OCH₃ | N | CH | C—OCH₃ | |
| 82 | 2-methyl-3-(CHF—CF₃)thien-3-yl | OCH₃ | N | CH | C—OCH₃ | |
| 83 | 2-methyl-3-(CF₃)pyridin-3-yl | OCH₃ | N | CH | C—OCH₃ | |
| 84 | 2-methyl-3-(CF=CF—CF₃)pyridin-3-yl | OCH₃ | N | CH | C—OCH₃ | |
| 85 | 2-methyl-3-(1,3-dioxolan-2-yl)thien-3-yl | OCH₃ | N | N | C—OCH₃ | |

TABLE 2-continued

Examples of the compounds of the formula (I)

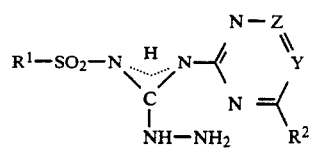

(I)

| Example No. | R¹ | R² | X | Y | Z | Melting point (°C.) |
|---|---|---|---|---|---|---|
| 86 | 3-methyl-2-(CF=CF—CF₃)-thiophene | OCH₃ | N | CH | C—OCH₃ | |
| 87 | 3-methyl-2-(CF=CF—CF₃)-thiophene | OCH₃ | N | N | C—OCH₃ | |
| 88 | 2-(4,5-dihydrothiazol-2-yloxy)-phenyl | OCH₃ | N | N | C—OCH₃ | |
| 89 | 7-methyl-naphthalen-2-yl | CH₃ | N | N | C—OCH₃ | |
| 90 | 6-bromo-2-methyl-3-CON(CH₃)₂-pyridin-4-yl | OCH₃ | N | CH | C—OCH₃ | |
| 91 | 2-methyl-phenyl-SO₂—NH—OCH₃ | OCH₃ | N | CH | C—OCH₃ | 208 |
| 92 | 2-methyl-phenyl-SO₂—NH—OCH₃ | OCH₃ | N | CH | C—CH₃ | |
| 93 | 2-methyl-phenyl-SO₂—NH—OCH₃ | OCH₃ | N | CH | C—C₂H₅ | |
| 94 | 2-methyl-phenyl-SO₂—NH—OCH₃ | CF₃ | N | CH | C—OCH₃ | |

TABLE 2-continued

Examples of the compounds of the formula (I)

$$R^1-SO_2-N\overset{H}{\underset{C}{\vphantom{|}}}\!\!\!-N=\!\!\!\overset{N-Z}{\underset{N\,=\!\!\!=}{\vphantom{|}}}\!\!\!\!\overset{Y}{\underset{R^2}{\vphantom{|}}}\quad (I)$$
$$\underset{NH-NH_2}{|}$$

| Example No. | R¹ | R² | X | Y | Z | Melting point (°C.) |
|---|---|---|---|---|---|---|
| 95 | 2-($SO_2-NH-OCH_3$)-phenyl | $CH_3$ | N | CH | $C-CH_3$ | |
| 96 | 2-($SO_2-NH-OCH_3$)-phenyl | $CH_3$ | N | N | $C-CH_3$ | |
| 97 | 2-($SO_2-NH-OCH_3$)-phenyl | $CH_3$ | N | N | $C-OCH_3$ | 230 |
| 98 | 2-($SO_2-NH-OCH_3$)-phenyl | $CH_3$ | N | N | $C-OC_2H_5$ | |
| 99 | 2-($SO_2-NH-OCH_3$)-phenyl | $C_2H_5$ | N | N | $C-OCH_3$ | |
| 100 | 2-($SO_2-NH-OCH_3$)-phenyl | $C_2H_5$ | N | N | $C-OC_2H_5$ | |
| 101 | 2-($SO_2-NH-OCH_3$)-phenyl | $NHCH_3$ | N | N | $C-OC_2H_5$ | |
| 102 | 2-($SO_2-NH-OCH_3$)-phenyl | $NHCH_3$ | N | N | $C-OCH_3$ | |
| 103 | 2-($SO_2-NH-OCH_3$)-phenyl | $OCHF_2$ | N | CH | $C-OCHF_2$ | |

TABLE 2-continued

Examples of the compounds of the formula (I)

$$R^1-SO_2-N\underset{NH-NH_2}{\overset{H}{\underset{C}{\mid}}}N=\underset{R^2}{\overset{N-Z}{\underset{N}{\mid}}}Y$$  (I)

| Example No. | R¹ | R² | X | Y | Z | Melting point (°C.) |
|---|---|---|---|---|---|---|
| 104 | 2-(SO₂—NH—OCH₃)-phenyl | CH₃ | N | CH | C—OCHF₂ | |
| 105 | 2-(SO₂—NH—OCH₃)-phenyl | Cl | N | CH | C—OCHF₂ | |
| 106 | 2-(SO₂—NH—OCH₃)-phenyl | CH₃ | N | CH | C—OC₂H₅ | |
| 107 | 2-(SO₂—NH—OCH₃)-phenyl | OCH₃ | N | CH | C—NHCH₃ | |
| 108 | 2-(SO₂—NH—OCH₃)-phenyl | OCH₃ | N | CH | C—OCHF₂ | |
| 109 | 2-(SO₂—NH—OCH₃)-phenyl | CF₃ | N | CH | C—NHCH₃ | |
| 110 | 2-(SO₂N(CH₃)₂)-phenyl | CH₃ | N | CH | C—OCH₃ | 165 |
| 111 | 4-COOC₂H₅, 5-CH₃, 1-CH₃-pyrazol-3-yl | CH₃ | N | CH | C—OCH₃ | 105 |
| 112 | 2-Cl-phenyl | CH₃ | N | CH | C—CH₃ | 139 |

TABLE 2-continued

Examples of the compounds of the formula (I)

$$R^1-SO_2-N\overset{H}{\underset{\underset{NH-NH_2}{\overset{|}{C}}}{\cdots}}N=\overset{N-Z}{\underset{N}{\overset{\|}{\underset{R^2}{Y}}}}$$ (I)

| Example No. | R¹ | R² | X | Y | Z | Melting point (°C.) |
|---|---|---|---|---|---|---|
| 113 | 2-(OCF₃)C₆H₄ | CH₃ | N | N | C—N(CH₃)₂ | 246 |
| 114 | 2-Cl-C₆H₄ | CH₃ | N | N | C—N(CH₃)₂ | 163 |
| 115 | 2-(OCH₃)C₆H₄ | CH₃ | N | N | C—N(CH₃)₂ | 132 |
| 116 | 2-(OCHF₂)C₆H₄ | CH₃ | N | N | C—N(CH₃)₂ | 197 |
| 117 | 2-(C₆H₅)C₆H₄ | CH₃ | N | N | C—OCH₃ | 162 |
| 118 | 2-(CF₃)C₆H₄ | CH₃ | N | N | C—SCH₃ | 216 |
| 119 | 3-methyl-2-(COOCH₃)-thienyl | OCH₃ | N | CH | C—OCH₃ | 163 |
| 120 | 2-(OCF₃)C₆H₄ | CH₃ | N | CH | C—CH₃ | 60 |
| 121 | 2-(SO₂N(CH₃)₂)C₆H₄ | CH₃ | N | CH | C—CH₃ | 172 |

TABLE 2-continued

Examples of the compounds of the formula (I)

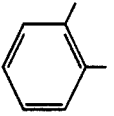

| Example No. | R¹ | R² | X | Y | Z | Melting point (°C.) |
|---|---|---|---|---|---|---|
| 122 | 2-F-phenyl | CH₃ | N | CH | C—CH₃ | 159 |
| 123 | 2-(N(CH₃)(OCH₃)SO₂)-phenyl | CH₃ | N | CH | C—CH₃ | 197 |
| 124 | 2-(COOCH₃)-phenyl | H | N | CH | C—CH₃ | |
| 125 | 2-(COOCH₂CH₂Cl)-phenyl | H | N | CH | C—CH₃ | |
| 126 | 2-(OCF₃)-phenyl | H | N | CH | C—CH₃ | |
| 127 | 2-(COOC₂H₅)-phenyl | H | N | CH | C—CH₃ | |
| 128 | 2-(COOCH₃)-phenyl | CH₂OCH₃ | N | CH | C—OCH₃ | |

Preparation of the compound of Example 112 (see Table 2):

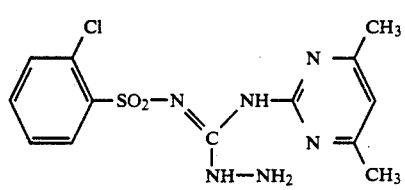

0.4 g (8.2 mmol) of hydrazine hydrate are added to a solution of 3.4 g (8.2 mmol) of N'-(4,6-dimethyl-pyrimidin-2-yl)N''-(2-chloro-phenylsulphonyl)-O-phenyl-isourea in 50 ml of tetrahydrofuran. The reaction mixture is stirred for 30 minutes at 20° to 25° C., then poured onto 250 ml of ice-water; the organic products are extracted with dichloromethane. The organic phase is separated, washed with water, dried with sodium sulphate and filtered. The filtrate is evaporated in vacuo and the solid residue is recrystallized from isopropanol.

2.0 g (69% of theory) of N'-(4,6-dimethyl-pyrimidin-2-yl)-N''-amino-N'''-(2-chloro-phenylsulphonyl)-guanidine of melting point 139° C. are obtained.

USE EXAMPLES

In the following Use Examples, the compound listed below is used as comparison substance:

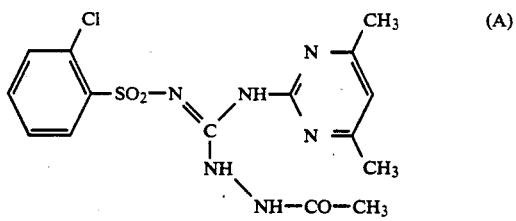

N'-(4,6-Dimethyl-pyrimidin-2-yl)-N''-acetylamino-N'''-(2-chloro-phenylsulphonyl)-guanidine (disclosed in EP-A 121,082).

EXAMPLE A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, for example, the compounds in accordance with Preparation Examples 2, 3, 4, 7, 110, 111 and 112 show a clearly superior activity compared with the prior art.

EXAMPLE B

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, for example, the compounds in accordance with Preparation Examples 1, 2, 3, 4, 5, 6, 7, 110, 111 and 112 show a clearly superior activity compared with the prior art.

It will be appreciated that the instant specification and claims are set forth by way of illustration and not limitation, and that various modifications and changes may be made without departing from the spirit and scope of the present invention.

What is claimed is:

1. An aminoguanidinoazine of the formula

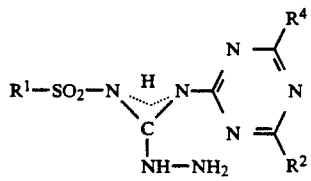

in which
$R^1$ stands for the radical

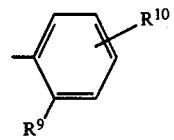

where
$R^9$ stands for fluorine, chlorine, bromine, methyl, trifluoromethyl, methoxy, difluoromethoxy, trifluoromethoxy, $C_1$-$C_3$-alkylthio, $C_1$-$C_3$-alkylsulphinyl, $C_1$-$C_3$-alkylsulphonyl, dimethylaminosulphonyl, diethylaminosulphonyl, N-methoxy-N-methylamino-sulphonyl, phenyl, phenoxy or $C_1$-$C_3$-alkoxycarbonyl and
$R^{10}$ stands for hydrogen or chlorine; where furthermore
$R^1$ stands for the radical

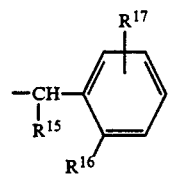

where
$R^{15}$ stands for hydrogen,
$R^{16}$ stands for fluorine, chlorine, bromine, methyl, methoxy, ethoxy, difluoromethoxy, trifluoromethoxy, methoxycarbonyl, ethoxycarbonyl, methylsulphonyl or dimethylaminosulphonyl and
$R^{17}$ stands for hydrogen or chlorine; where furthermore
$R^1$ stands for the radical

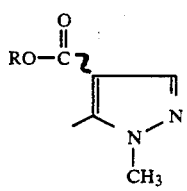

where
R stands for $C_1$-$C_2$-alkyl; in which furthermore
$R^1$ stands for the radical

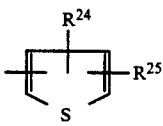

where
$R^{24}$ and $R^{25}$ are identical or different and stand for hydrogen, fluorine, chlorine, bromine, cyano, nitro, $C_1$-$C_4$-alkyl (which is optionally substituted by fluorine, chlorine, $C_1$-$C_4$-alkoxy and/or $C_1$-$C_4$-halogenoalkoxy), $C_1$-$C_4$-alkoxy (which is optionally substituted by fluorine and/or chlorine), $C_1$-$C_4$-alkylthio, $C_1$-$C_4$-alkylsulphinyl or $C_1$-$C_4$-alkylsulphonyl (which is optionally substituted by fluorine and/or chlorine), di-($C_1$-$C_4$-alkyl)-aminosulphonyl, $C_1$-$C_4$-alkoxycarbonyl, dioxolanyl or 2-thiazolyl, $R^2$ stands for hydrogen, fluorine, chlorine, bromine, methyl, dimethoxymethyl, trifluoromethyl, methoxy, ethoxy, difluoromethoxy, methylthio, ethylthio, amino, methylamino, ethylamino, dimethylamino, diethylamino or methoxymethyl, and $R^4$ stands for hydrogen, fluorine, chlorine, bromine, methyl, trifluoromethyl, methoxy, ethoxy, propoxy, isopropoxy, difluoromethoxy, methylthio, ethylthio, methylamino, ethylamino, dimethylamino or diethylamino.

2. A compound according to claim 1, wherein such compound is N'-(4-methoxy-6-methyl-s-triazin-2-yl)-N''-amino-N''''-(2-trifluoromethoxy-phenylsulphonyl)-guanidine of the formula

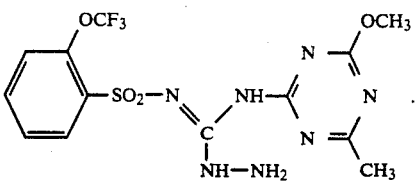

3. A compound according to claim 1, wherein such compound is N'-(4,6-dimethoxy-s-triazin-2-yl)-N''-amino-N''''-(2-trifluoromethoxy-phenylsulphonyl)-guanidine of the formula

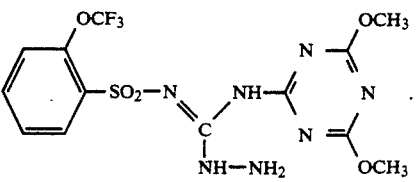

4. A herbicidal composition comprising a herbicidally effective amount of a compound or salt according to claim 1 and a diluent.

5. A method of combating unwanted vegetation which comprises applying to such vegetation or to a locus from which it is desired to exclude such vegetation a herbicidally effective amount of a compound or salt according to claim 1.

6. The method according to claim 5, wherein such compound is

N'-(4-methoxy-6-methyl-s-triazin-2yl)-N''-amino-N''''-(2-trifluoromethoxy-phenylsulphonyl)guanidine, or N'-(4,6-dimethoxy-s-triazin-2-yl)-N''-amino-N''''-(2-trifluoromethoxy-phenylsulfonyl)guanidine, or a salt thereof.

* * * * *